United States Patent [19]

Springmann

[11] Patent Number: 5,872,305

[45] Date of Patent: Feb. 16, 1999

[54] METHOD FOR PREPARING A TEST GAS STREAM

[75] Inventor: Thomas Springmann, Freiburg, Germany

[73] Assignee: Testo GmbH & Co., Lenzkirch, Germany

[21] Appl. No.: 904,806

[22] Filed: Aug. 1, 1997

[30] Foreign Application Priority Data

Aug. 1, 1996 [DE] Germany ............... 196 31 002.4

[51] Int. Cl.$^6$ ............................................. G01N 1/22
[52] U.S. Cl. ................ 73/23.31; 73/23.41; 422/83; 422/94
[58] Field of Search ............... 73/23.31, 23.41, 73/23.42; 422/83, 94

[56] References Cited

U.S. PATENT DOCUMENTS

| 3,593,023 | 7/1971 | Dodson et al. ............ 73/23.31 X |
| 5,410,907 | 5/1995 | Ström et al. ................ 73/23.31 |
| 5,543,113 | 8/1996 | Koike et al. .............. 73/23.31 X |

FOREIGN PATENT DOCUMENTS

| 41 00 363 A1 | 7/1992 | Germany . | |
| 277536 | 12/1987 | Japan ............... | 73/23.31 |
| 315027 | 11/1992 | Japan ............... | 73/23.31 |
| 281186 | 10/1993 | Japan ............... | 73/23.31 |

OTHER PUBLICATIONS

Reuther, "Topical Report: Interlaboratory Program to Validate a Protocal For the Measurement of $NO_2$ Emissions From Rangetop Burners", Gas Research Institute, Dec. 1994.

*Primary Examiner*—Daniel S. Larkin
*Attorney, Agent, or Firm*—Foley, Hoag & Eliot LLP

[57] ABSTRACT

A method for preparing a test gas stream for a gas analyzer in which test gas is drawn from a test gas stream by a test gas probe, conducted through a test gas tube to a condensate separator, and then analyzed in the gas analyzer for certain components such as $NO_2$ and $SO_2$ for example, with the average flow rate of the test gas stream in the test gas tube being set to a value of at least 1.5 m/s.

19 Claims, 2 Drawing Sheets

METHOD FOR PREPARING A TEST GAS STREAM

BACKGROUND OF THE INVENTION

1. Field of the Invention

This invention relates to a method for preparing a test gas stream for a gas analyzer, and more particularly to a method for preparing a test gas stream for a gas analyzer in which a test gas is drawn out of an exhaust stream by a test gas probe, fed through a test gas tube to a condensate separator, and then analyzed by a gas analyzer.

2. Description of the Related Art

To analyze flue gases from a furnace or exhaust from an engine such as a gas engine, a test gas stream is tapped off the main exhaust stream by a test gas probe and conducted through a test gas tube to a condensate separator prior to analysis in the gas analyzer. Analysis of the gas is then performed either directly or with the interposition of another, longer lead, located downstream from the condensate separator. Gas analysis requires that the test gas be prepared, especially to remove the moisture contained in the gas.

During the transport of the test gas from the probe to the condensate separator, there is the danger that, because of the effects of cooling, the condensate will precipitate prematurely on the inside wall of the test gas tube, and consequently more test gas will come in contact with the liquid condensate. When this happens, gas components such as $NO_2$ and $SO_2$ may become partially bonded in the condensate thereby causing the concentration of these components to change as the gas flows through the test gas tube. This variation can affect the value of these gas components measured by the analyzer and the resulting accuracy of the analyzer, since the measured concentration may differ from the concentration actually present in the exhaust of the flue gas.

To avoid such measurement errors, it is known, for example from German Patent Application 42 16 404 A1, to heat the test gas tube. By heating the test gas tube, the test gas may be maintained at a temperature above the dew point as it flows through the device to prevent premature precipitation of the condensate.

In these devices, condensate separation takes place completely in the condensate separator located downstream from the test gas tube. By limiting the condensation region, it is possible to ensure that the condensate can precipitate rapidly along a short distance in the gas flow path so that the period of time during which the test gas comes in contact with the liquid condensate is limited. Components such as $NO_2$ and $SO_2$ are thus given only limited opportunity to bond with the condensate so that minimal distortion of the measurement results occurs.

Although this type of gas preparation has proven successful in theory, there are problems in practice, particularly in that a relatively large amount of energy must be expended to heat the test gas tube, especially since the tube may extend over a relatively long distance. In addition, the condensate separator located downstream must be subjected to considerable cooling because the test gas must be cooled in the condensate chamber to a temperature below the dew point. Since cooling to avoid measurement error is intended to take place over a distance that is as short as possible, the cooling power that must be provided is very high. This high energy consumption is particularly problematic in portable and mobile gas analyzers designed for use by chimney sweeps and furnace technicians, since portable gas analyzers typically run on batteries. The duration during which the gas analyzer can be operated is therefore very limited and spare batteries must be carried if the measuring tasks that occur during a conventional workday are to be performed.

Attempts to overcome this problem have previously been directed toward reducing the amount of energy required to heat the test gas tube. These efforts have typically involved providing the test gas tube with an insulating jacket to minimize heat loss to the environment. Unfortunately, providing an insulating jacket of this nature results in test gas tubes which are relatively heavy and awkward to handle.

SUMMARY OF THE INVENTION

Accordingly, one objective of this invention is to improve the method for preparing a test gas to reduce the amount of energy required to operate the gas analyzer. A further objective of this invention is to improve the method of preparing a test gas to increase the operating time of battery-operated gas analyzers. A yet further objective is to provide a method of preparing a test gas which enables the weight of the gas analyzer to be minimized.

To achieve these and other objectives, this invention provides a method for preparing a test gas stream for a gas analyzer in which test gas is drawn out of an exhaust stream by a test gas probe, fed through a test gas tube to a condensate separator, and then certain components, such as $NO_2$ and $SO_2$, are analyzed in the gas analyzer. In this method, the average flow rate of the test gas stream in the test gas tube is set to a value of at least 1.5 m/s.

The invention is based on the idea of completely eliminating heating of the test gas tube and largely preventing absorption of $NO_2$ and $SO_2$, by increasing the throughput rate of the test gas to minimize its residence time in the test gas tube. By increasing the throughput rate, it no longer becomes necessary to provide an insulating jacket around the test gas tube, thus enabling a thin walled gas tube to be utilized to minimize the weight of the gas analyzer.

Another energy-saving effect is that the test gas tube serves as a cooling section for the test gas so that with a suitable design, a temperature of the test gas at the end of the test gas tube can approach the ambient temperature. As a result, the cooling power required for cooling the test gas to a temperature below the dew point is also reduced. The cooling power is generally applied by a cooling element integrated into the condensate separator. Contrary to the previous situation in which a temperature drop of 200° to 300° C. had to be achieved in the condensate separator, by allowing the test gas to cool in the test gas tube, the temperature drop required to be achieved by the condensate separator in this method may be reduced to around 20° C. This comparatively low cooling power can also be applied over a considerably shorter distance, with the result that the condensate separator can be reduced significantly in size.

Specifically, this effect may be achieved when the average flow rate of the test gas stream, in other words averaged over the flow cross section, assumes a value of at least 1.5 m/s. It currently appears that the best results are achieved when the flow rate is set to a value in the range from 4.0 m/s and 7.0 m/s. Increases of the flow rate above about 7 m/s do not appear advantageous, since further reduction of the absorption of $NO_2$ and $SO_2$ no longer significantly influences the measurement results, while the flow resistance increases sharply with the consequence that a delivery pump with an increased power draw is required.

The conditions mentioned above for the flow rate also ensure that drops of condensate that precipitate on the walls of the tube cannot adhere to the walls of the test gas values, but are entrained by the stream of test gas and transported to the condensate chamber of the condensate separator.

For most of the measurement tasks that occur in practice, the measurement error caused by the absorption of $NO_2$ and $SO_2$ can be reduced to negligible levels if the average residence time of the test gas stream in the test gas tube is less than 3 seconds. A measurement error of less than 1% can be achieved if, according to a preferred variation on the method, the residence time is in the range from 0.25 sec to 1.0 sec.

Special advantages are obtained by using a test gas tube made of polytetrafluoroethylene sold under the trademark of TEFLON. This material is sufficiently resistant to aggressive components of the test gas and also has a surface structure that makes it difficult for condensate droplets to adhere, so that these droplets are especially easily entrained by the test gas stream.

Preferably, a test gas tube with an inside diameter in the range from 1.5 mm to 4.0 mm is used. More preferably, the inside diameter should be set to approximately 2.0 mm. The above diameter figures are adjusted to the measurement tasks described at the outset from the field of exhaust technology and also take into account the conventionally installed delivery capacity of the test gas pump that sucks the test gas stream out of the exhaust stream. This power permits a delivery volume of approximately 0.9 l/min. Taking into account the average data found for the state of the test gas as well as the flow resistances, the speed condition for the test gas stream described at the outset is obtained. A diameter of less than about 1.0 mm, under practical conditions, results in flow resistances that are so high that the installed pumping power is no longer sufficient. With an inside diameter of more than about 4.0 mm on the other hand, the flow rate in the test gas tube will already have been reduced to the point that significant measurement errors occur because of increased absorption of $NO_2$ and $SO_2$.

As far as the length of the test gas tube used is concerned, lengths been about 1.5 m and 5.0 m have proven advantageous. They can, of course, be varied if necessary to adjust the final temperature at the connection to the condensate separator. Usually a length of about 3 m is sufficient to ensure cooling to ambient temperature for conventional measuring tasks, depending on the thermal characteristics of the tube material and the geometric configuration of the tube.

One preferred variation on the method provides for using a condensate separator with an integrated Peltier element, with the cold side of the Peltier element being subjected directly to the flow of the test gas stream. A condensate separator of this kind is described in a new U.S. patent application filed Aug. 1, 1997, by Thomas Springmann, entitled CONDENSATE SEPARATOR, Ser. No. 08/904,714, the contents of which are hereby incorporated by reference. Such a condensate separator has considerably improved efficiency over previously known condensate separators, so that the total energy requirements associated with preparing the test gas may be greatly reduced.

BRIEF DESCRIPTION OF THE DRAWINGS

The preferred embodiments of the present invention will now be described more specifically with reference to the attached drawings, wherein.

DETAILED DESCRIPTION OF THE PREFERRED EMBODIMENTS

In test series, absorption of $NO_2$ and $SO_2$ in an unheated test gas tube made of TEFLON was studied. Keeping the tube length and other variables constant, the inside diameter was varied as shown in the following table and the resultant absorption of $NO_2$ and $SO_2$ was determined. Specifically, test gas was used with a concentration of 179 ppm $NO_2$ and 481 ppm $SO_2$, moistened by a flask containing water at 60° C. The dew point at the inlet was 60° C. and the dew point at the outlet was 23° C. (ambient conditions). The flow rate was set to a constant 0.9 l/min. Results of these experiments are set forth in the following table and are shown in graphical form in FIGS. 1 and 2.

TABLE

| Inside diameter (mm) | $NO_2$ absorption (%) | $SO_2$ absorption (%) |
| --- | --- | --- |
| 1.5 | .2 | .2 |
| 2 | .4 | .3 |
| 3 | 2.6 | .4 |
| 4 | 4.1 | 1.3 |
| 6 | 6 | 2 |

Figure 1:
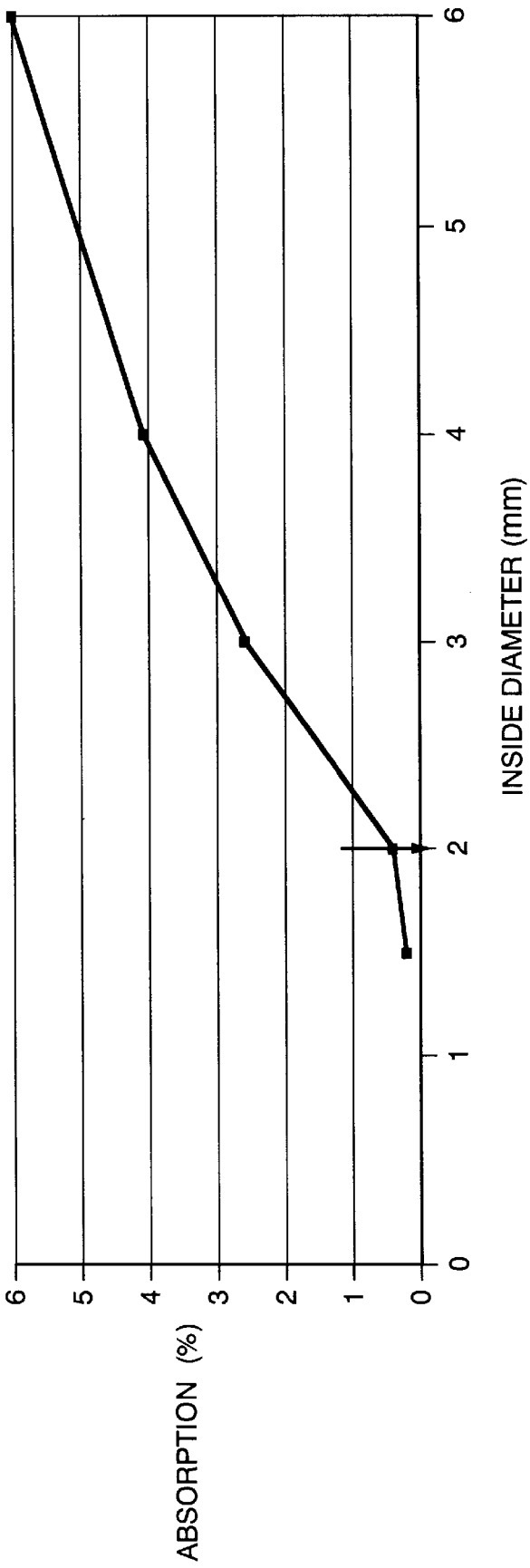
FIG. 1 is a graph showing the absorption of $NO_2$ as a function of the inside diameter of the test gas tube.

The graph shown in FIG. 1 shows absorption of $NO_2$ as a function of inside diameter of the test gas tube. Following an initially flat slope for absorption of 0.2% to 0.4%, the curve rises relatively steeply at the transition from an inside diameter of 1.5 mm to 2 mm, and then tapers off at larger diameter values. A 6 mm tube exhibited an absorption rate of 6%.

This graph suggests that it is advantageous to use a test gas tube having an inside diameter of about 2 mm under the given measuring conditions, since absorption is still low while the shielding resistance is still not very great.

The largest of the diameter values given (6 mm) corresponds to the diameter of the test gas lines previously used and illustrates the potential for improvement offered by the method according to this invention. This measured point also makes clear that in measuring tubes with currently conventional diameters, heating is unavoidable since absorption at the 6% level is unacceptable for most applications.

Figure 2:
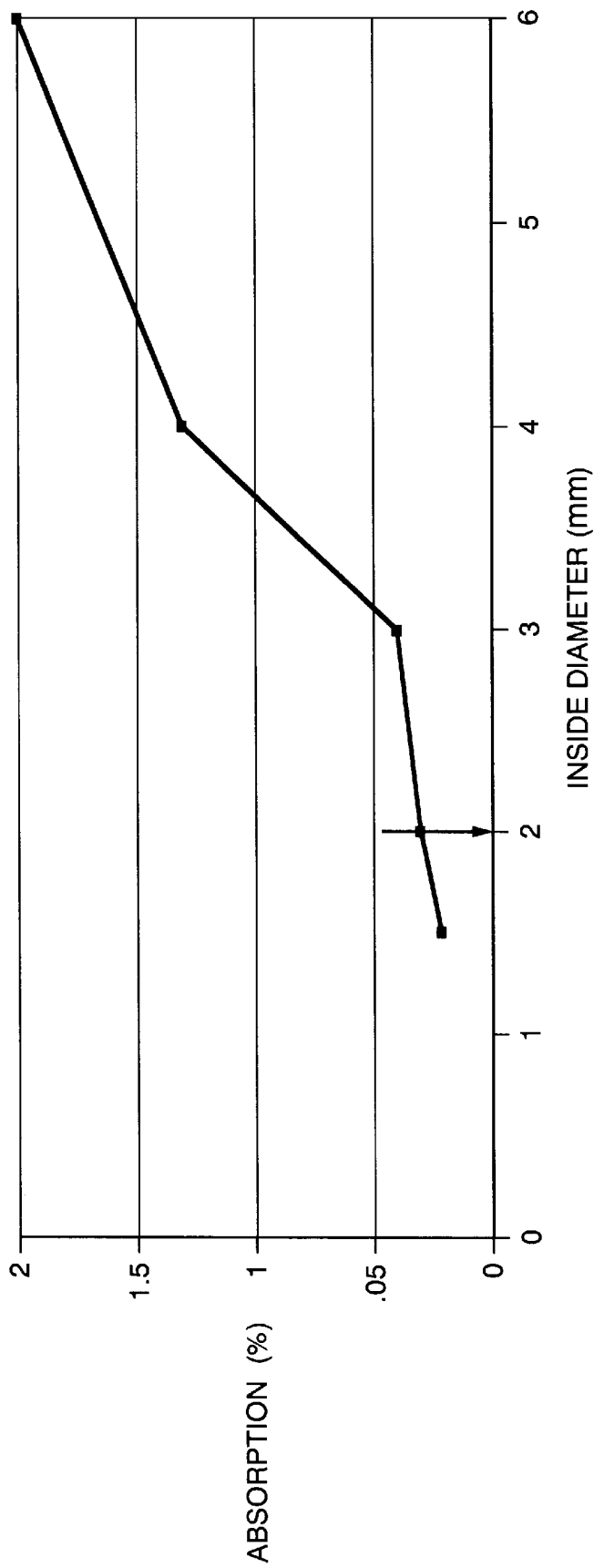
FIG. 2 is a graph showing the absorption of $SO_2$ as a function of the inside diameter of the test gas tube.

The graph shown in FIG. 2 shows absorption of $SO_2$ as a function of diameter similar to that described above. The curve is flat in the range from 1.5 mm to 3 mm, with absorption values between 0.2% and 0.4%. The absorption curve then rises very sharply toward larger diameters and reaches an absorption of 2% at the largest diameter tested. These findings suggest that it is advantageous to use a test tube with an inside diameter up to about 3 mm, as far as absorption of $SO_2$ is concerned. With the additional consideration of the absorption behavior of $NO_2$ it can be concluded that an inside diameter of up to about 2 mm is preferable.

These tests confirm that a tube with these dimensions is suitable for reliably preventing the deposition of condensate droplets on the inside wall. An accumulation of such droplets to form a so-called water trap through which the test gas must be passed can no longer result. The test gas tube is also position-independent, in other words it can be located anywhere, even suspended or overhead for example.

In addition, these tests confirm that the tested test gas tube is less sensitive to dirt. No intermediate cleaning was required during a continuous test that lasted two days. This is an indication of the practical reliability of the concept according to the invention.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art which this invention pertains.

What I claim is:

1. A method for preparing a test gas stream for a gas analyzer, comprising.

drawing a test gas from an exhaust stream by a test gas probe;

feeding the test gas through an unheated test gas tube at an average flow rate of at least 1.5 m/s to a condensate separator, wherein the test gas tube has a length sufficient to allow the test gas to cool to a temperature approaching ambient temperature upon entering the condensate separator; and analyzing the test gas to determine at least one of a $NO_2$ component and a $SO_2$ component.

2. A method according to claim 1, wherein the average flow rate is in the range from 4.0 m/s to 7.0 m/s.

3. A method according to claim 1, wherein an average residence time of the test gas stream in the test gas tube is less than 3.0 seconds.

4. A method according to claim 3, wherein the average residence time is between about 0.25 sec and 1.0 sec.

5. A method according to claim 3, wherein the test gas tube is made of polytetrafluoroethylene.

6. A method according to claim 5, wherein the test gas tube has an inside diameter in the range from 1.0 mm to 4.0 mm.

7. A method according to claimed 6, wherein the inside diameter of the test gas tube is approximately 2.0 mm.

8. A method according to claim 7, wherein a length of the test gas tube is between about 1.5 m and 5.0 m.

9. A method according to claim 1, wherein the test gas tube is made of polytetrafluoroethylene.

10. A method according to claim 1, wherein the test gas tube has an inside diameter in the range from 1.0 mm to 4.0 mm.

11. A method according to claim 1, wherein the test gas tube has an inside diameter of approximately 2.0 mm.

12. A method according to claim 1, wherein a length of the test gas tube is between about 1.5 m and 5.0 m.

13. A method according claim 1, further comprising a condensate separator cooled by an integrated Peltier element, a cold side of the Peltier element being exposed to the test gas stream.

14. A method for preparing a test gas stream for a gas analyzer, comprising;

drawing a test gas from an exhaust stream by a test gas probe;

feeding the test gas through an unheated polytetrafluoroethylene test gas tube having an inside diameter in the range from 1.0 mm to 4.0 mm at an average flow rate of at least 1.5 m/s to a condensate separator such that an average residence time of the test gas stream in the test gas tube is less than 3.0 seconds, wherein the test gas tube has a length sufficient to allow the test gas to cool to a temperature approaching ambient temperature upon entering the condensate separator; and analyzing the test gas to determine at least one of a $NO_2$ component and a $SO_2$ component.

15. A method according to claim 14, wherein the average flow rate is in the range from 4.0 m/s to 7.0 m/s.

16. A method according to claim 14, wherein the average residence time is between about 0.25 sec and 1.0 sec.

17. A method according to claim 14, wherein the inside diameter of the test gas tube is approximately 2.0 mm. mm.

18. A method according to claim 14, wherein a length of the test gas tube is between about 1.5 m and 5.0 m.

19. A method according claim 14, wherein the condensate separator is cooled by an integrated Peltier element, a cold side of the Peltier element being exposed to the test gas stream.

* * * * *